(12) United States Patent
Ott et al.

(10) Patent No.: US 6,496,958 B1
(45) Date of Patent: Dec. 17, 2002

(54) YIELD PREDICTION AND STATISTICAL PROCESS CONTROL USING PREDICTED DEFECT RELATED YIELD LOSS

(75) Inventors: Reinhold Ott, Richmnond, VA (US); Herbert Lammering, Glen Allen, VA (US); Heinrich Ollendorf, Richmond, VA (US)

(73) Assignee: Infineon Technologies Richmond, LP, Sandston, VA (US)

( * ) Notice: Subject to any disclaimer, the term of this patent is extended or adjusted under 35 U.S.C. 154(b) by 0 days.

(21) Appl. No.: 09/299,979

(22) Filed: Apr. 27, 1999

(51) Int. Cl.[7] ........................... G06F 17/50; G06F 19/00
(52) U.S. Cl. ............................. 716/4; 700/121
(58) Field of Search ................. 716/4, 19, 20, 716/21, 1, 2; 700/108, 109, 110, 121

(56) References Cited

U.S. PATENT DOCUMENTS

| | | | | |
|---|---|---|---|---|
| 3,751,647 A | * | 8/1973 | Maeder et al. | 235/151.11 |
| 5,544,256 A | * | 8/1996 | Brecher et al. | 382/149 |
| 5,777,901 A | * | 7/1998 | Berezin et al. | 364/578 |
| 6,265,232 B1 | * | 7/2001 | Simmons | 438/14 |

* cited by examiner

*Primary Examiner*—Matthew Smith
*Assistant Examiner*—Leigh Marie Garbowski
(74) *Attorney, Agent, or Firm*—Stanton Braden

(57) ABSTRACT

In accordance with the present invention, a method, which may be implemented by employing a program storage device, for determining yield loss for a device includes the steps of determining killing probabilities corresponding to values of inspection parameters based on historic inspection information, determining defects on the device and ordering the defects by classifying the defects according to the inspection parameters. The defects adopt the killing probabilities associated with the same values of the inspection parameters. The method further includes the step of calculating a predicted yield loss based on the defects and the adopted killing probabilities. The method further includes the step of applying statistical process control to the predicted yield loss for all in-line inspection (process) steps.

34 Claims, 3 Drawing Sheets

YIELD PREDICTION AND STATISTICAL PROCESS CONTROL USING PREDICTED DEFECT RELATED YIELD LOSS

BACKGROUND

1. Technical Field

This disclosure relates to yield prediction and production control and more particularly, to a method for determining yield for semiconductor fabrication processes.

2. Description of the Related Art

A common standard exists in the semiconductor industry where wafers are inspected at various times by optical and other inspection tools during production. As a result, a process engineer obtains a number of defects per wafer, x and y coordinates of each defect and a set of parameters (different for different tools) specific for each particular defect. Any irregularities, such as structural imperfections, particles, residuals or embedded foreign material are considered as defects. Defect data collected by laser scanning, optical or SEM in-line defect inspections during the production of modern semiconductor devices are comprised of events with absolutely different yield impact. Overall this total count information does not enable the process engineer to assign a yield loss to defects detected at a certain process step.

In-line Statistical Process Control (SPC) is performed after the total defect count is provided by the inspection tool directly, or after yield loss estimations are provided from automated or manual review information (for example, from an optical microscope or SEM). Because high defect counts do not necessarily indicate high yield detraction, the previously described methodology is not an optimized process control. The additional review after yield loss estimations (manual and/or automated) requires additional human resources, extends the process time and postpones information feedback to the process units.

Considering killing probabilities of any of the detected defects (probability p of the defect to kill the entire chip), the total defect count is comprised of events with all values of killing probabilities between 0 and 1. The count information on its own (even including further characterization of each single defect by optical microscopes, scanning electron microscopes (SEM), atomic force microscopes (AFM), energy-dispersive X-ray spectroscopy (EDX) (either manual review or automated defect classification)) is not sufficient to assign an accurate number of yield loss to this process part for complex chip designs (e.g., numerous redundancies on memory products). Therefore, this number of yield loss is not a good value to be used for an effective production control. To obtain useful yield impact information, it is indispensable to correlate the actual defect data to electrical fails. Waiting for the electrical data, however, delays the feedback to the process units by weeks or months. Therefore, the immediate correct interpretation of the in-line inspection data is essential to approach high productivity.

A real time yield prediction methodology without additional optical review uses historic data for a given process step to calculate one average killing probability for all defects. The detected number of defects or number of defective dies (dies including one or more defects) on a certain wafer is multiplied by this number. As a result, the engineer obtains the number of killed chips. This methodology is only applicable and accurate for single wafers if the wafer contains a normal defect pareto for this process step. The methodology is questionable because excursions in the defect count trend typically do not follow the standard pareto for each layer.

Therefore, a need exists for an optimized control process considering all available information for any single detected defect which may include statistical process or production control for real time yield impact information on semiconductor devices. A further need exists for an automated method which does not require manual defect classification.

SUMMARY OF THE INVENTION

In accordance with the present invention, a method, which may be implemented by employing a program storage device, for determining yield loss for a device includes the steps of determining killing probabilities corresponding to values of inspection parameters based on historic inspection information, determining defects on the device, classifying the defects according to the inspection parameters, the defects adopting the killing probabilities associated with the same values of the inspection parameters and calculating a predicted yield loss based on the defects and the adopted killing probabilities.

In other methods, which may be implemented by employing a program storage device, the step of determining defects on the device may include the step of inspecting the device using inspection tools. The step of classifying the defects may include the steps of determining defect inspection parameters used to determine each defect, finding corresponding values of the defect inspection parameters with the values of the inspection parameters determined based on historic information, and associating the killing probability of the values of the inspection parameters determined based on historic information with each defect having the corresponding values. The method may further include the step of calculating a predicted yield loss for each of a plurality of inspection processes. The step of calculating a predicted yield loss for each of a plurality of inspection processes may be performed by calculating the predicted yield loss according to the equation $$\Delta Y_k = 1 - \prod_{ij} (1 - kp_{kij} n_{kij})$$

where $\Delta Y_k$ is the predicted yield loss for a process k, $kp_k$ is the adopted killing probability for a defect $n_k$ and i and j are counters. The method may include the step of calculating an overall predicted yield loss based on the predicted yield loss of the plurality of inspection processes. The step of calculating an overall predicted yield loss based on the predicted yield loss of the plurality of inspection processes may be performed by calculating the overall predicted yield loss according to the equation $$\Delta Y = 1 - \prod_k (1 - \Delta Y_k)$$

where $\Delta Y_k$ is the predicted yield loss for a process k and $\Delta Y$ is the overall predicted yield loss. The method may include the step of graphically representing the predicted yield loss. The step of classifying the defects may be performed automatically by a machine, such as a computer. This avoids manually inspection and classification. The step of applying statistical process control to the predicted yield loss is preferably included.

Another method, which may be implemented by employing a program storage device, for determining yield loss for semiconductor wafers includes the steps of creating a parametric space defined by values of at least two inspection parameters, assigning killing probabilities corresponding to values of the at least two inspection parameters based on historic inspection information, inspecting the semiconductor device to determine defects on the semiconductor device, and ordering the defects on the semiconductor device by classifying the defects according to the at least two inspection parameters. The classified defects adopt the killing probabilities of the parametric space to which the defects are assigned. The step of calculating a predicted yield loss based on the defects and the adopted killing probabilities is also included.

In other methods, which may be implemented by employing a program storage device, the step of creating a parametric space defined by values of at least two inspection parameters may further include the steps of forming an m-dimensional space by providing m inspection parameters, the m-dimensional space including subspaces, and assigning values of each of the m inspection parameters to each subspace such that each subspace represents one of a given value and a range of values for each of the m inspection parameters. The step of inspecting the semiconductor device to determine defects on the semiconductor device may include the steps of inspecting the semiconductor device using inspection tools, and generating a results file. The results file includes defect size and location information and other inspection parameters for each defect. The step of classifying the defects may be performed automatically by a machine. This avoids manually inspection and classification. The step of applying statistical process control to the predicted yield loss is preferably included. The step of ordering the defects may include the steps of determining defect inspection parameters used to determine each defect, finding corresponding values of the defect inspection parameters with the values of the at least two inspection parameters determined based on historic information, and associating the killing probability of the values of the at least two inspection parameters determined based on historic information with each defect having the corresponding values.

In still other methods, which may be implemented by employing a program storage device, the step of calculating a predicted yield loss for each of a plurality of inspection processes may be included. The step of calculating a predicted yield loss for each of a plurality of inspection processes may be performed by calculating the predicted yield loss according to the equation $$\Delta Y_k = 1 - \prod_{ij} (1 - kp_{kij} n_{kij})$$

where $\Delta Y_k$ is the predicted yield loss for a process k, $kp_k$ is the adopted killing probability for a defect $n_k$ and i and j are counters. The method may include the step of calculating an overall predicted yield loss based on the predicted yield loss of the plurality of inspection processes. The step of calculating an overall predicted yield loss based on the predicted yield loss of the plurality of inspection processes may be performed by calculating the overall predicted yield loss according to the equation $$\Delta Y = 1 - \prod_{k} (1 - \Delta Y_k)$$

where $\Delta Y_k$ is the predicted yield loss for a process k and $\Delta Y$ is the overall predicted yield loss. The method may include the step of graphically representing the predicted yield loss.

Another method, which may be implemented by employing a program storage device for determining yield loss for semiconductor wafers includes the steps of computing killing probabilities based on historic data for subspaces in a parameter space, the parameter space being divided in to subspaces by values of inspection parameters, inspecting the semiconductor wafer to generate defect information in accordance with predetermined inspection parameters, and ordering defects by determining defect inspection parameters used to determine each defect and finding corresponding subspaces to assign the defects. The method also includes the steps of associating the killing probability of each subspace to the defects assigned to the subspace, determining a predicted yield loss for each of a plurality of inspection processes based on a number of defects in each subspace and the killing probability assigned to each subspace, and determining an overall predicted yield loss for the semiconductor wafer based on the predicted yield loss for each of the plurality of inspection processes.

In other methods, which may be implemented by employing a program storage device, the step of determining a predicted yield loss for each of a plurality of inspection processes may be performed by calculating the predicted yield loss according to the equation $$\Delta Y_k = 1 - \prod_{ij} (1 - kp_{kij} n_{kij})$$

where $\Delta Y_k$ is the predicted yield loss for a process k, $kp_k$ is the killing probability for a defect $n_k$ in a subspace ij, where i and j represent counters for a two dimensional parameter space. The step of calculating an overall predicted yield loss may be performed by calculating the overall predicted yield loss according to the equation $$\Delta Y = 1 - \prod_{k} (1 - \Delta Y_k)$$

where $\Delta Y_k$ is the predicted yield loss for a process k and $\Delta Y$ is the overall predicted yield loss. The method may further include the step of graphically representing the predicted yield loss and the overall predicted yield loss. The step of classifying the defects may be performed automatically by a machine, such as a computer. This avoids manually inspection and classification. The step of applying statistical process control to the predicted yield loss per process step ($\Delta Y_k$) is preferably included.

These and other objects, features and advantages of the present invention will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF PREFERRED EMBODIMENTS

Figure 1:
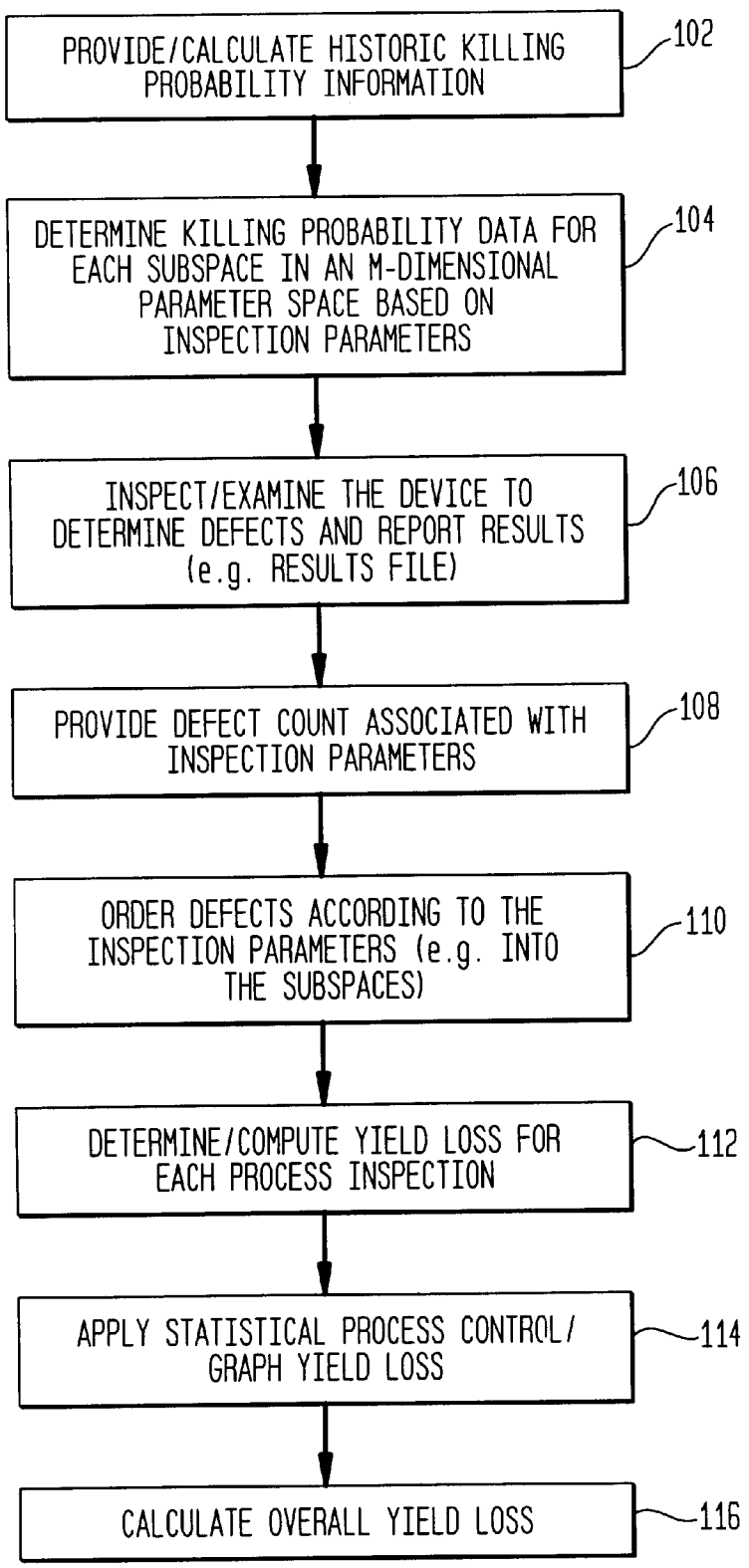
FIG. 1 is a block/flow diagram for a method/system for determining real time yield loss in accordance with the present invention.

The present invention relates to yield prediction and production control for semiconductor fabrication inspections. More particularly, the present invention relates to a method for determining yield loss in real time for semiconductor chips/wafers during fabrication processes. Through the correlation of in-line defect data with pre-fuse electrical data, the present invention is able to predict yield loss for each defect-inspected wafer immediately after in-line inspection with high accuracy. Using parameters assigned to each defect, specific for each of the used defect inspection tools, for example as KLA-Tencor 2135, Applied Materials-Orbot WF736, KLA-Tenor AIT or others, the present invention is able to treat uncommon defect paretos on single wafers in a correct and accurate manner. This method enables the prediction of yield loss in real time with high accuracy, for all inspected wafers immediately after in-line inspections. The method in accordance with the present invention further provides statistical process control for considering calculated predicted yield loss information.

One advantage of the present method is that high accuracy levels are achieved, for a fully automated quantitative real time yield prediction for any single inspected wafer, even with uncommon defect paretos (graphs). Statistical process control (SPC) is applied on the calculated predicted yield loss. SPC may include techniques known in the art.

To achieve the most accurate yield loss prediction for single wafers, the parameters assigned by inspection tools for each single defect are employed. Assuming an inspection tool assigns m different parameters to each defect, all inspected defects will be distributed in an m-dimensional parameter space. Defects with similar killing probabilities will cluster in certain areas called subspaces. Subspaces are defined in the m-dimensional parameter space such that defects with similar killing probability appear in the same subspace (this method may be compared to a classification at an optical or SEM microscope where defects with similar optical appearance are grouped in classes of defects). One advantage of the method in accordance with the present invention is that the present invention can be fully automated. This means that manual defect classification is not needed. Defects with similar killing probability may include defects with different optical appearance. By sorting the defects by assigned inspection parameters the standard deviation of the killing probability distribution of all defects in one subspace of the parameter space is tightened and therefore the yield loss prediction is optimized. This methodology does not need additional reviewing resources and provides the predicted yield loss in real time.

Semiconductor wafers include a plurality of chips. Defects found on the wafer (and therefore chips) have killing probabilities which are used to predict how many and which chips are to be rejected due to defects or failures.

It should be understood that the elements shown in FIG. 1 may be implemented in various forms of hardware, software or combinations thereof. Preferably, these elements are implemented in software on one or more appropriately programmed general purpose digital computers having a processor and memory and input/output interfaces. Referring now in specific detail to the drawings in which like reference numerals identify similar or identical elements throughout the several views, and initially to FIG. 1, a block/flow diagram for a system/method for predicting yield loss in real time is shown. In a block 102, killing probability information $kp_{ij}$ is determined. In preferred embodiments, killing probability information $kp_{ij}$ is determined as described in a commonly assigned disclosure entitled "SYSTEM AND METHOD FOR DETERMINING YIELD IMPACT FOR SEMICONDUCTOR DEVICES", U.S. patent application Ser. No. 09/228,178, filed Jan. 11, 1999, incorporated herein by reference. The method to obtain the killing probability $kp_{ij}$ information may alternatively be any method that provides historic killing probability data, as long as the method considers single defects and their characteristics. Historic killing probability data may include data on defects and positions thereof on semiconductor wafers previously inspected and tested. Historic killing probability data is maintained to determine trends and/or processing problems in the semiconductor fabrication/inspection process.

In block 104, killing probability, $kp_{ij}$, is determined based on the killing probability information or data of block 102. In accordance with the invention, the killing probability is calculated based on historic data and is determined for each subspace in an m-dimensional parameter space. This killing probability is based on two or more inspection tool parameters. For given values of the two or more parameters, subspaces are created corresponding to the values of the parameters. Based on historic killing probability data having the given values, a killing probability is assigned for each subspace.

Figure 2:
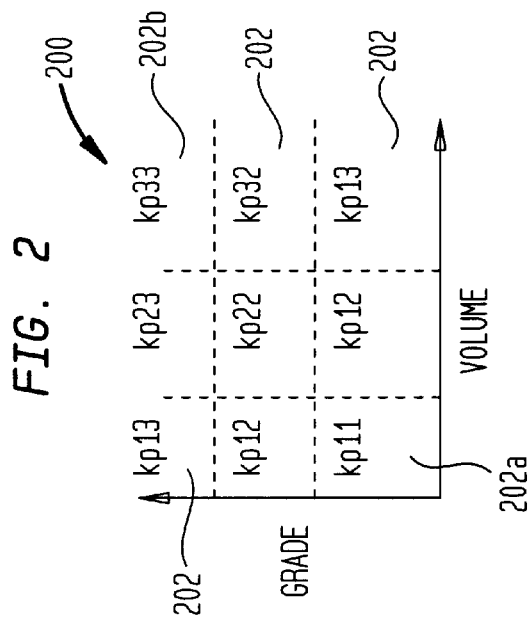
FIG. 2 is a two dimensional parameter space for charting killing probabilities based on historic data in accordance with inspection parameters for the present invention.

As shown in FIG. 2, an m-dimensional parameter space 200 is illustratively shown where m equals 2. Parameter space 200 includes a plurality of subspaces 202. Each subspace 202 includes representations of historic data having similar killing probabilities, $kp_{ij}$. Then, $kp_{ij}$ represents killing probabilities in a column i and a row j in parameter space 200. In this example, a subspace 202a includes a killing probability, $kp_{11}$. Likewise, a subspace 202b includes a killing probability, $kp_{33}$. Subspaces 202 are arranged according to parameters in the m-dimensional parameter space. In this example, m equals 2 and the 2 parameters are Grade and Volume. Grade is a measure of the intensity of the scattered light at a particular defect, and Volume is a measure of x and y sizes of the defect. Other inspections parameters may be used, and these parameters may be different from inspection device to inspection device. As shown in FIG. 2, historic information is organized to provide easy access to specific information in accordance with the present invention. In this example, for a given value or range of values of Grade and a given value or range of values of Volume, a certain number of defects are determined corresponding to these values. The defects provide a killing probability as determined in the previously referenced commonly assigned disclosure entitled "SYSTEM AND METHOD FOR DETERMINING YIELD IMPACT FOR SEMICONDUCTOR DEVICES". This killing probability is assigned to a subspace indicated in the 2 parameter space. This is done for each subspace.

Returning now to FIG. 1, in block 106, a semiconductor wafer is inspected for defects using an in-line inspection tool. This inspection is performed between processing steps (i.e., in-line) during the fabrication of the semiconductor device. In-line inspection tools are known in the art and may include an Orbot WF 730 series, available commercially from Applied Materials, Inc., a Tencor AIT or Tencor 7000 or KLR 2100 series available commercially from KLA-Tencor, Inc. The in-line inspection tool generates a result file which displays the results of the inspection as well as specific tool parameters. In an illustrative example, an Orbot WF 736 Duo inspection tool, available commercially from Applied Materials, Inc., is employed for inspecting a wafer. The inspection tool generates a standard results file, for example, a standard KLA-Tencor results file. A partial results file of this type is illustratively shown in FIG. 3.

Figure 3:
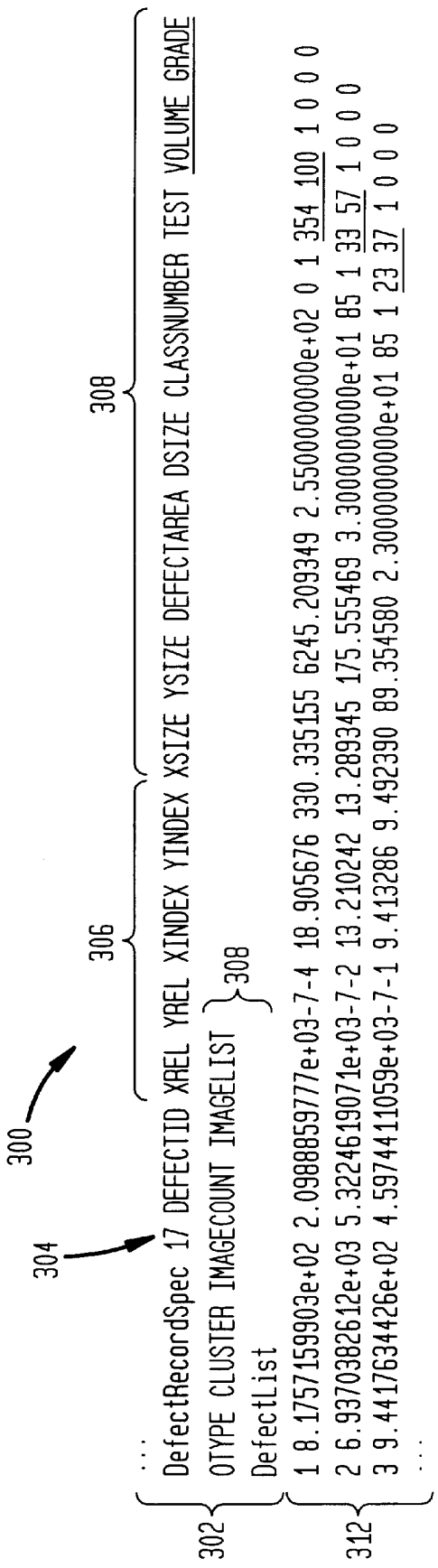
FIG. 3 is a partial results file generated after an inspection to provide defect data to be used in accordance with the present invention.

Referring to FIG. 3, a results file 300 is shown in a standard format. A parameter list 302 includes defect identification information 304, defect location information 306 and defect characteristic information 308. A defect list 312 is also included which has actual data (defect coordinates) and parameter information corresponding to the parameter list 302. Note that the defect parameter information for volume and grade is underlined in the parameter list 302 and the defect list 312.

Returning again to FIG. 1, in a block 108, using a most up to date results file (e.g., results file 300 of FIG. 3), an actual defect count is obtained. The actual defect count of the semiconductor wafer is comprised of defects with killing probabilities varying between 0 and 1. A number of defects for each wafer inspected may be recorded in chart as shown in FIG. 4.

Figure 4:
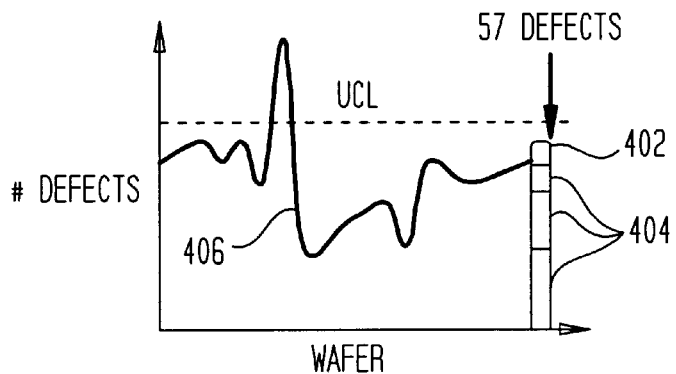
FIG. 4 is a graph showing a number of defects for each process inspection for a wafer in accordance with the present invention.

Referring to FIG. 4, a plot or graph 400 of number of defects for each process step of an inspected wafer is shown. This graph shows a number of defects (actual defect count) for each inspection process. A height of bar 402 gives an overall number of defects for each process step for a given wafer. For a particular wafer, the total number of defects in a given process is illustratively 57 as indicated in FIG. 4. Bar 402 may include segments 404. Each segment 404 may represent defects from a set of inspection parameters for a given process step in the semiconductor wafer fabrication process. When the number of defects for all process steps are connected a graph 406 is generated. A UCL line is indicated which represents an upper control limit. Wafers with calculated yield loss above this limit are considered out of control and must wait for disposition. Other graphical or tabular representations for the number of defects may also be useful. The data of graph 406 will be used as described herein.

Figure 5:
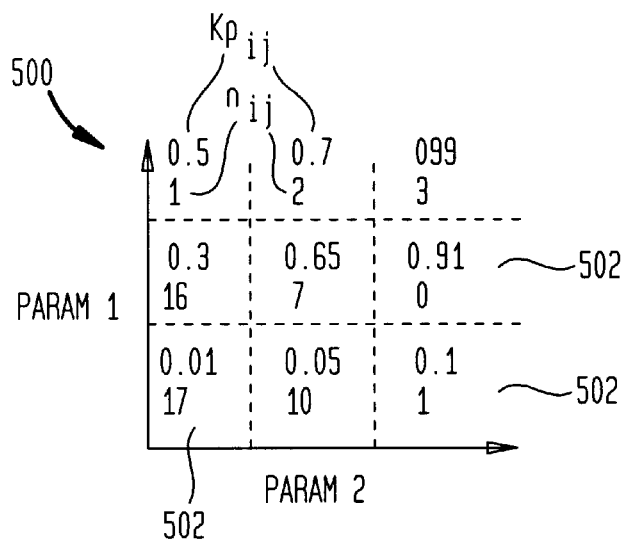
FIG. 5 is an illustrative two dimensional parameter space showing killing probabilities and number of defects for each subspace in accordance with the present invention.

Referring again to FIG. 1, in a block 110, defects from a current wafer which is being considered are ordered in accordance with inspection tool parameters. For example, the defects as determined by the inspection tool are illustratively ordered according to grade and volume as shown in FIG. 5. In this way, the given defects are now associated with the assigned killing probabilities as determined in block 104. Since the present invention classifies defects according to subspaces which are based on inspection parameters, the entire process is capable of automation, i.e., no manual classification is needed since all inspection parameters associated with each individual defect are assigned and recorded using the inspection tools. This saves a significant amount of time.

Referring to FIG. 5, a 2-dimensional parameter space 500 is shown having ordered defects according to grade and volume. Each subspace 502 has a killing probability associated therewith. Each subspace 502 represents a particular killing probability $kp_{ij}$, and a number of defects $n_{ij}$ are assigned to each subspace 502 according to the inspection parameters. In this way, the particular killing probability in each subspace 502 is assigned to the defects which are placed according to values of grade and volume (other parameters may be used) in that subspace 502. Although 9 subspaces are illustratively shown more or less subspaces 502 may be used. $kp_{ij}$ and $n_{ij}$ may be given for a single process and represented by $kp_{kij}$ and $n_{kij}$. From parameter space 500, a total number of defects for a given process step k may be calculated according to the formula:

$$N_k = \sum_i \sum_j n_{kij} \qquad \text{(EQ. 1)}$$

Referring again to FIG. 1, a yield loss is calculated for the current wafer in block 112. The yield loss is a defect related yield loss for the process step k. The yield loss may be calculated by the following formula:

$$\Delta Y_k = 1 - \prod_{ij}(1 - kp_{kij}n_{kij}) \qquad \text{(EQ. 2)}$$

$kp_{kij}$ and $n_{kij}$ are determined for each subspace in a parameter space, and entered in EQ. 2 for calculation of yield loss $\Delta Y_k$ for a process step k.

In a block 114, statistical process control is applied to the yield loss $\Delta Y_k$ calculated in block 112. This yields a new graph or chart for predicted yield loss which takes into account the number of defects as well as the respective killing probability for each individual defect (see EQ. 2) for all process steps (all k's). The chart includes a more accurate representation of wafer yield than the conventional techniques. The disposition of wafers or lots of wafers may be more accurately categorized with respect to the defects determined by in-line inspection tools. This permits statistical process control (SPC) based on predicted yield loss immediately after in-line wafer inspections for all in-line inspection (process) steps. In conventional techniques, this data is generally not available until all electrical testing has been performed on the wafers. Advantageously, the present invention applies statistical process control (SPC) in real time which saves time and money.

Figure 6:
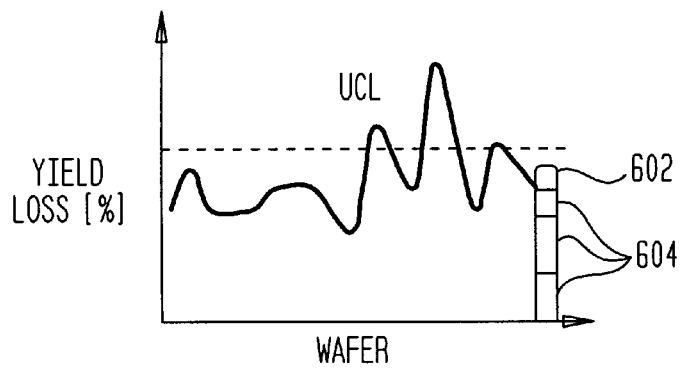
FIG. 6 is a graph showing a yield loss for each process inspection for a wafer in accordance with the present invention.

Referring to FIG. 6, a chart or graph 600 is illustratively shown in accordance with the present invention. Using the data used to generate graph 400 in FIG. 4, a graph 600 is calculated for each inspection process for a given wafer. A bar 602 is generated for each process. A height of bar 602 gives an overall predicted yield loss for that process step. Yield loss for each subspace may be given by segments 604 of bar 602. Segments 604 accumulate to give the overall yield loss for each process step. When the yield losses for all the process steps are connected a graph 606 is generated. A UCL line is indicated. Other graphical or tabular representations for yield loss may also be useful.

Referring again to FIG. 1, in a block 116, an overall yield loss $\Delta Y$ may be calculated directly from the following:

$$\Delta Y = 1 - \prod_k (1 - \Delta Y_k) \qquad \text{(EQ. 3)}$$

$\Delta Y$ is calculated for all inspection processes (all k's) for a given wafer. In this way, yield loss may be determined in real time without waiting over extended periods of time to amass historical data to make yield loss calculations as performed in prior art techniques.

The present invention provides significant advantages over the prior art. Among these advantages are the capability for automating defect classification in accordance with inspection parameters. All classifying may advantageously be performed without manual inspection or classification. The present invention also permits yield loss prediction immediately after in-line inspection thereby providing real time information about the inspected wafers without before electrical testing. Although the present invention has been described in terms of semiconductor in-line process inspection, the present invention is broader and may be applicable to other areas. These other areas may include fabrication processes where multiple systems or parts are inspected and defect data is available. The present invention may then be employed to generate real time yield loss for the products being fabricated.

Having described preferred embodiments for yield prediction and statistical process control using predicted defect related yield loss (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for determining yield loss for a device comprising the steps of:
   determining killing probabilities corresponding to values of inspection parameters based on historic inspection information;
   determining defects on the device;
   classifying the defects according to the inspection parameters, the defects adopting the killing probabilities associated with the same values of the inspection parameters; and
   calculating a predicted yield loss for each of a plurality of inspection processes based on the defects and the adopted killing probabilities.

2. The method as recited in claim 1, wherein the step of determining defects on the device includes the step of inspecting the device using inspection tools.

3. The method as recited in claim 1, wherein the step of classifying the defects includes the steps of:
   determining defect inspection parameters used to determine each defect;
   finding corresponding values of the defect inspection parameters with the values of the inspection parameters determined based on historic information; and
   associating the killing probability of the values of the inspection parameters determined based on historic information with each defect having the corresponding values.

4. The method as recited in claim 1 wherein the step of calculating a predicted yield loss for each of a plurality of inspection processes is performed by calculating the predicted yield loss according to the equation:

$$\Delta Y_k = 1 - \prod_{ij} (1 - k p_{kij} n_{kij})$$

where $\Delta Y_k$ is the predicted yield loss for a process k, $kp_k$ is the adopted killing probability for a defect $n_k$ and i and j are counters.

5. The method as recited in claim 1, further comprising the step of calculating an overall predicted yield loss based on the predicted yield lose of the plurality of inspection processes.

6. The method as recited in claim 5, wherein the step of calculating an overall predicted yield loss based on the predicted yield loss of the plurality of inspection processes is performed by calculating the overall predicted yield loss according to the equation:

$$\Delta Y = 1 - \prod_{k} (1 - \Delta Y_k),$$

where $\Delta Y_k$ is the predicted yield loss for a process k and $\Delta Y$ is the overall predicted yield loss.

7. The method as recited in claim 1, further comprising the step of graphically representing the predicted yield loss.

8. The method as recited in claim 1, wherein the step of classifying the defects is performed automatically by a machine.

9. The method as recited in claim 1, further comprising the step of applying statistical process control to the predicted yield loss.

10. A method as defined in claim 1 wherein said classifying is performed automatically.

11. A method for determining yield loss for semiconductor wafers comprising the steps of:
    creating a parametric space defined by values of at least two inspection parameters;
    assigning killing probabilities corresponding to values of the at least two inspection parameters based on historic inspection information;
    inspecting the semiconductor device to determine defects on the semiconductor device;
    ordering the defects on the semiconductor device by classifying the defects according to the at least two inspection parameters, the classified defects adopting th killing probabilities of the parametric space to which the defects are assigned: and
    calculating a predicted yield loss for each of a plurality of inspection processes based on the defects and the adopted killing probabilities.

12. The method as recited in claim 11, wherein the step of creating a parametric space defined by values of at least two inspection parameters further comprises the steps of:
    forming an m-dimensional space by providing m inspection parameters, the m-dimensional space including subspaces; and
    assigning values of each of the m inspection parameters to each subspace such that each subspace represents one of a given value and a range of values for each of the m inspection parameters.

13. The method as recited in claim 11, wherein the step of inspecting the semiconductor device to determine defects on the semiconductor device includes the steps of:
    inspecting the semiconductor device using inspection tools; and
    generating a results file, the results file including defect size and location information and other inspection parameter information.

14. The method as recited in claim 11, wherein the step of ordering the defects includes the steps of:
    determining defect inspection parameters used to determine each defect;
    finding corresponding values of the defect inspection parameters with the values of the at least two inspection parameters determined based on historic information; and associating the killing probability of the values of the at least two inspection parameters determined based on historic information with each defect having the corresponding values.

15. The method as recited in claim 11 wherein the step of calculating a predicted yield loss for each of a plurality of inspection processes is performed by calculating the predicted yield loss according to the equation:

$$\Delta Y_k = 1 - \prod_{ij}(1 - kp_{kij}n_{kij})$$

where $\Delta Y_k$ is the predicted yield loss for a process k, $kp_k$ is the adopted killing probability for a defect $n_k$ and i and j are counters.

16. The method as recited in claim 11, further comprising the step of calculating an overall predicted yield loss based on the predicted yield loss of the plurality of inspection processes.

17. The method as recited in claim 16, wherein the step of calculating an overall predicted yield loss based on the predicted yield loss of the plurality of inspection processes is performed by calculating the overall predicted yield loss according to the equation:

$$\Delta Y = 1 - \prod_{k}(1 - \Delta Y_k)$$

where $\Delta Y_k$ is the predicted yield loss for a process k and $\Delta Y$ is the overall predicted yield loss.

18. The method as recited in claim 11, further comprising the step of graphically representing the predicted yield loss.

19. The method as recited in claim 11, wherein the step of ordering the defects is performed automatically by a machine.

20. The method as recited in claim 11, further comprising the step of applying statistical process control to the predicted yield loss.

21. A method as defined in claim 11 wherein said ordering by classifying is performed automatically.

22. A method for determining yield loss for semiconductor wafers comprising the steps of:
   computing killing probabilities based on historic data for subspaces in a parameter space, the parameter space being divided in to subspaces by values of inspection parameters;
   inspecting the semiconductor wafer to generate defect information in accordance with predetermined inspection parameters;
   ordering defects by determining defect inspection parameters used to determine each defect and finding corresponding subspaces to assign the defects;
   associating the killing probability of each subspace to the defects assigned to the subspace;
   determining a predicted yield loss for each of a plurality of inspection processes based on a number of defects in each subspace and the killing probability assigned to each subspace;
   applying statistical process control to the predicted yield loss; and
   determining an overall predicted yield loss for the semiconductor wafer based on the predicted yield loss for each of the plurality of inspection processes.

23. The method as recited in claim 22, wherein the step of determining a predicted yield loss for each of a plurality of inspection processes is performed by calculating the predicted yield loss according to the equation:

$$\Delta Y_k = 1 - \prod_{ij}(1 - kp_{kij}n_{kij})$$

where $\Delta Y_k$ is the predicted yield loss for a process k, $kp_k$ is the killing probability for a defect $n_k$ in a subspace ij, where i and j represent counters for a two dimensional parameter space.

24. The method as recited in claim 22, wherein the step of calculating an overall predicted yield loss is performed by calculating the overall predicted yield loss according to the equation:

$$\Delta Y = 1 - \prod_{k}(1 - \Delta Y_k)$$

where $\Delta Y_k$ is the predicted yield loss for a process k and $\Delta Y$ is the overall predicted yield loss.

25. The method as recited in claim 22, further comprising the step of graphically representing the predicted yield loss and the overall predicted yield loss.

26. The method as recited in claim 22, wherein the step of ordering the defects is performed automatically by a machine.

27. A program storage device readable by machine, tangibly embodying a program of instructions executable by the machine to perform method steps for determining yield loss for a device, the method steps comprising;
   determining killing probabilities corresponding to values of inspection parameters based on historic inspection information;
   determining defects on the device;
   classifying the defects according to the inspection parameters, the defects adopting the killing probabilities associated with the same values of the inspection parameters; and
   calculating a predicted yield loss for each of a plurality of inspection processes based on the defects and the adopted killing probabilities.

28. The program storage device as recited in claim 27, wherein the step of classifying the defects includes the steps of:
   determining defect inspection parameters used to determine each defect;
   finding corresponding values of the defect inspection parameters with the values of the inspection parameters determined based on historic information; and
   associating the killing probability of the values of the inspection parameters determined based on historic information with each defect having the corresponding values.

29. The program storage device as recited in claim 27 wherein the step of calculating a predicted yield loss for each of a plurality of inspection processes is performed by calculating the predicted yield loss according to the equation:

$$\Delta Y_k = 1 - \prod_{ij}(1 - kp_{kij}n_{kij})$$

where $\Delta Y_k$ is the predicted yield loss for a process k, $kp_k$ is the adopted killing probability for a defect $n_k$ and i and j are counters.

30. The program storage device as recited in claim 27, further comprising the step of calculating an overall predicted yield loss based on the predicted yield loss of the plurality of inspection processes.

31. The program storage device as recited in claim 30, wherein the step of calculating an overall predicted yield loss based on the yield loss of the plurality of inspection processes is performed by calculating the overall predicted yield loss according to the equation:

$$\Delta Y = 1 - \prod_{k}(1 - \Delta Y_k)$$

where $\Delta Y_k$ is the predicted yield loss for a process k and $\Delta Y$ is the overall predicted yield loss.

32. The program storage device as recited in claim 27, wherein the step of classifying the defects is performed automatically by a machine.

33. The program storage device as recited in claim 27, further comprising the step of applying statistical process control to the predicted yield loss.

34. A program storage device as defined in claim 27 wherein said classifying is performed automatically.

* * * * *